(12) United States Patent
Zabar et al.

(10) Patent No.: US 12,035,968 B2
(45) Date of Patent: *Jul. 16, 2024

(54) SYSTEM FOR TISSUE ABLATION USING PULSED LASER

(71) Applicant: Eximo Medical Ltd., Rehovot (IL)

(72) Inventors: Yoel Zabar, Nes Ziona (IL); Oren Meshulam Stern, Shilo (IL); Ilan Ben Oren, Modi'in (IL)

(73) Assignee: EXIMO MEDICAL LTD., Rehovot (IL)

( * ) Notice: Subject to any disclaimer, the term of this patent is extended or adjusted under 35 U.S.C. 154(b) by 0 days.

This patent is subject to a terminal disclaimer.

(21) Appl. No.: 18/458,516

(22) Filed: Aug. 30, 2023

(65) Prior Publication Data

US 2024/0058059 A1 Feb. 22, 2024

Related U.S. Application Data

(63) Continuation of application No. 17/395,799, filed on Aug. 6, 2021, now abandoned, which is a
(Continued)

(51) Int. Cl.
*A61B 18/24* (2006.01)
*A61B 17/00* (2006.01)
(Continued)

(52) U.S. Cl.
CPC .............. *A61B 18/245* (2013.01); *G02B 6/04* (2013.01); *G02B 6/4296* (2013.01);
(Continued)

(58) Field of Classification Search
CPC ........ A61B 18/245; A61B 2017/00274; A61B 2017/00778; A61B 2017/320044;
(Continued)

(56) References Cited

U.S. PATENT DOCUMENTS 4,641,912 A 2/1987 Goldenberg
4,732,448 A 3/1988 Goldenberg
(Continued)

FOREIGN PATENT DOCUMENTS

CA 3017252 C 12/2019
CA 3105728 A1 1/2020
(Continued)

*Primary Examiner* — Jonathan T Kuo
(74) *Attorney, Agent, or Firm* — Kevin P. Radigan, Esq.; HESLIN ROTHENBERG FARLEY & MESITI, P.C.

(57) ABSTRACT

Systems for enabling delivery of very high peak power laser pulses through optical fibers for use in ablation procedures preferably in contact mode. Such lasers advantageously emit at 355 nm wavelength. Other systems enable selective removal of undesired tissue within a blood vessel, while minimizing the risk of damaging the blood vessel itself, based on the use of the ablative properties of short laser pulses of 320 to 400 nm laser wavelength, with selected parameters of the mechanical walls of the tubes constituting the catheter, of the laser fluence and of the force that is applied by the catheter on the tissues. Additionally, a novel method of calibrating such catheters is disclosed, which also enables real time monitoring of the ablation process. Additionally, novel methods of protecting the fibers exit facets are disclosed.

20 Claims, 4 Drawing Sheets

Related U.S. Application Data continuation of application No. 17/123,205, filed on Dec. 16, 2020, now Pat. No. 11,090,117, which is a continuation of application No. 17/076,032, filed on Oct. 21, 2020, now Pat. No. 11,116,573, which is a continuation of application No. 15/309,193, filed as application No. PCT/IL2015/050529 on May 18, 2015, now abandoned.

(60) Provisional application No. 62/006,389, filed on Jun. 2, 2014, provisional application No. 61/994,904, filed on May 18, 2014.

(51) Int. Cl.

| | | |
|---|---|---|
| *A61B 17/32* | (2006.01) | |
| *A61B 18/00* | (2006.01) | |
| *A61B 18/22* | (2006.01) | |
| *A61N 5/06* | (2006.01) | |
| *A61N 5/067* | (2006.01) | |
| *G02B 6/04* | (2006.01) | |
| *G02B 6/42* | (2006.01) | |
| *H01S 3/109* | (2006.01) | |
| *H01S 3/16* | (2006.01) | |

(52) U.S. Cl.
CPC ............... *A61B 2017/00274* (2013.01); *A61B 2017/00778* (2013.01); *A61B 2017/320044* (2013.01); *A61B 2018/00345* (2013.01); *A61B 2018/00488* (2013.01); *A61B 2018/00494* (2013.01); *A61B 2018/00505* (2013.01); *A61B 2018/00559* (2013.01); *A61B 2018/00577* (2013.01); *A61B 2018/00601* (2013.01); *A61B 2018/00785* (2013.01); *A61B 2018/2211* (2013.01); *A61B 2218/002* (2013.01); *A61N 2005/0602* (2013.01); *A61N 2005/0609* (2013.01); *A61N 2005/061* (2013.01); *A61N 2005/0611* (2013.01); *A61N 2005/063* (2013.01); *A61N 2005/0661* (2013.01); *A61N 5/067* (2021.08); *H01S 3/109* (2013.01); *H01S 3/1611* (2013.01); *H01S 3/1643* (2013.01)

(58) Field of Classification Search
CPC ........... A61B 2018/00345; A61B 2018/00488; A61B 2018/00494; A61B 2018/00505; A61B 2018/00559; A61B 2018/00577; A61B 2018/00601; A61B 2018/00785; A61B 2018/2211; A61B 2218/002; A61B 2018/2247; G02B 6/04; G02B 6/4296; A61N 5/067; A61N 2005/0602; A61N 2005/0609; A61N 2005/061; A61N 2005/0611; A61N 2005/063; A61N 2005/0661; H01S 3/109; H01S 3/1611; H01S 3/1643; H01S 3/11
See application file for complete search history.

(56) References Cited

U.S. PATENT DOCUMENTS

| | | |
|---|---|---|
| 6,547,757 B1 | 4/2003 | Kranz |
| 7,931,659 B2 | 4/2011 | Bose |
| 7,976,533 B2 | 7/2011 | Larsson |
| 8,246,580 B2 | 8/2012 | Hopkins |
| 8,366,735 B2 | 2/2013 | Bose |
| 8,460,312 B2 | 6/2013 | Bose |
| 8,486,051 B2 | 7/2013 | Larsson |
| 8,915,896 B2 | 12/2014 | Sanders |
| 9,119,656 B2 | 9/2015 | Bose |
| 9,119,907 B2 | 9/2015 | Sherman |
| 9,199,011 B2 | 12/2015 | Locke |
| 9,655,633 B2 | 5/2017 | Leynov |
| 9,662,478 B2 | 5/2017 | Browd |
| 9,681,882 B2 | 6/2017 | Garrison |
| 9,820,761 B2 | 11/2017 | Garrison |
| 9,844,485 B2 | 12/2017 | Locke |
| 9,855,374 B2 | 1/2018 | Sherman |
| 9,864,140 B2 | 1/2018 | Adler |
| 9,883,877 B2 | 2/2018 | Look |
| 9,925,316 B2 | 3/2018 | Sanders |
| 10,166,375 B2 | 1/2019 | Browd |
| 10,201,315 B2 | 2/2019 | Peatfield |
| 10,226,263 B2 | 3/2019 | Look |
| 10,391,275 B2 | 8/2019 | Burnett |
| 10,702,292 B2 | 7/2020 | Look |
| 10,716,583 B2 | 7/2020 | Look |
| 10,722,253 B2 | 7/2020 | Deville |
| 10,765,592 B2 | 9/2020 | Locke |
| 10,835,647 B2 | 11/2020 | Sherman |
| 10,835,711 B2 | 11/2020 | Yang |
| 10,993,731 B2 | 5/2021 | Leynov |
| 11,051,832 B2 | 7/2021 | Look |
| 11,197,683 B1 | 12/2021 | Teigen |
| 11,247,030 B2 | 2/2022 | Browd |
| 11,259,821 B2 | 3/2022 | Buck |
| 11,317,787 B2 | 5/2022 | Hillman |
| 11,337,712 B2 | 5/2022 | Teigen |
| 11,357,951 B2 | 6/2022 | Burnett |
| 11,369,435 B2 | 6/2022 | Khan |
| 11,400,255 B1 | 8/2022 | Chou |
| 11,406,402 B2 | 8/2022 | Deville |
| 11,432,835 B2 | 9/2022 | Shaffer |
| 11,464,528 B2 | 10/2022 | Brady |
| 11,471,582 B2 | 10/2022 | Yee |
| 11,490,909 B2 | 11/2022 | Look |
| 11,497,521 B2 | 11/2022 | Mallaby |
| 11,547,426 B2 | 1/2023 | Deville |
| 11,835,707 B2 | 12/2023 | Liang |
| 2002/0095087 A1 | 7/2002 | Mourad |
| 2003/0171691 A1 | 9/2003 | Ward |
| 2004/0236228 A1 | 11/2004 | Stoltz |
| 2006/0229515 A1 | 10/2006 | Sharareh |
| 2007/0016068 A1 | 1/2007 | Grunwald |
| 2007/0073268 A1 | 3/2007 | Goble |
| 2007/0149985 A1 | 6/2007 | Cole |
| 2008/0082091 A1 | 4/2008 | Rubtsov |
| 2008/0177183 A1 | 7/2008 | Courtney |
| 2009/0048607 A1 | 2/2009 | Rockley |
| 2011/0060300 A1 | 3/2011 | Weig |
| 2013/0310680 A1 | 11/2013 | Werahera |
| 2014/0188062 A1 | 7/2014 | James |
| 2015/0238091 A1 | 8/2015 | Iyer |
| 2015/0320480 A1 | 11/2015 | Cosman, Jr. |
| 2016/0029902 A1 | 2/2016 | Smith |
| 2016/0135883 A1 | 5/2016 | Herscher |
| 2017/0100142 A1 | 4/2017 | Look |
| 2018/0028794 A1 | 2/2018 | Browd |
| 2018/0207397 A1 | 7/2018 | Look |
| 2019/0216476 A1 | 7/2019 | Barry |
| 2019/0290815 A1 | 9/2019 | Antonicelli |
| 2019/0343445 A1 | 11/2019 | Burnett |
| 2020/0022711 A1 | 1/2020 | Look |
| 2020/0179576 A1 | 6/2020 | Wood |
| 2020/0179578 A1 | 6/2020 | Look |
| 2020/0206457 A1 | 7/2020 | Boling |
| 2020/0281610 A1 | 9/2020 | Look |
| 2020/0289722 A1 | 9/2020 | Culbert |
| 2020/0337772 A1 | 10/2020 | Ben-Oren |
| 2021/0038306 A1 | 2/2021 | McLoughlin |
| 2021/0069467 A1 | 3/2021 | Garrison |
| 2021/0093756 A1 | 4/2021 | Sherman |
| 2021/0109340 A1 | 4/2021 | Kaicheng |
| 2021/0315598 A1 | 10/2021 | Buck |
| 2022/0008090 A1 | 1/2022 | Look |
| 2022/0031930 A1 | 2/2022 | Downey |
| 2022/0096104 A1 | 3/2022 | Ogle |
| 2022/0152345 A1 | 5/2022 | Simiele |
| 2022/0152346 A1 | 5/2022 | Burnett |
| 2022/0176031 A1 | 6/2022 | Cheng |
| 2022/0193366 A1 | 6/2022 | Cheng |

(56) References Cited

U.S. PATENT DOCUMENTS

| | | |
|---|---|---|
| 2022/0211437 A1 | 7/2022 | Ben-Oren |
| 2022/0218365 A1 | 7/2022 | Deville |
| 2022/0257268 A1 | 8/2022 | Culbert |
| 2022/0280171 A1 | 9/2022 | Teigen |
| 2022/0338887 A1 | 10/2022 | Nair |
| 2022/0339338 A1 | 10/2022 | Nair |
| 2022/0339339 A1 | 10/2022 | Nair |
| 2022/0378443 A1 | 12/2022 | Look |
| 2022/0378450 A1 | 12/2022 | Culbert |
| 2022/0379081 A1 | 12/2022 | Look |
| 2022/0379082 A1 | 12/2022 | Look |
| 2022/0379083 A1 | 12/2022 | Look |
| 2022/0379084 A1 | 12/2022 | Look |
| 2022/0379085 A1 | 12/2022 | Look |
| 2022/0379086 A1 | 12/2022 | Look |
| 2022/0387052 A1 | 12/2022 | Look |
| 2022/0387752 A1 | 12/2022 | Look |
| 2022/0387753 A1 | 12/2022 | Look |
| 2023/0026412 A1 | 1/2023 | Teigen |
| 2023/0099283 A1 | 3/2023 | Deville |
| 2023/0100426 A1 | 3/2023 | Deville |
| 2023/0301708 A1 | 9/2023 | Mickelsen |
| 2023/0329780 A1 | 10/2023 | Liu |
| 2023/0408329 A1 | 12/2023 | Zabar |

FOREIGN PATENT DOCUMENTS

| | | |
|---|---|---|
| CN | 112533550 A | 3/2021 |
| EP | 3423124 A4 | 10/2019 |
| EP | 3806757 A4 | 5/2022 |
| JP | 2021532850 A | 12/2021 |
| KR | 20210035811 A | 4/2021 |
| WO | 03057060 A1 | 7/2003 |
| WO | 2017155994 A1 | 9/2017 |
| WO | 2018019829 A1 | 2/2018 |

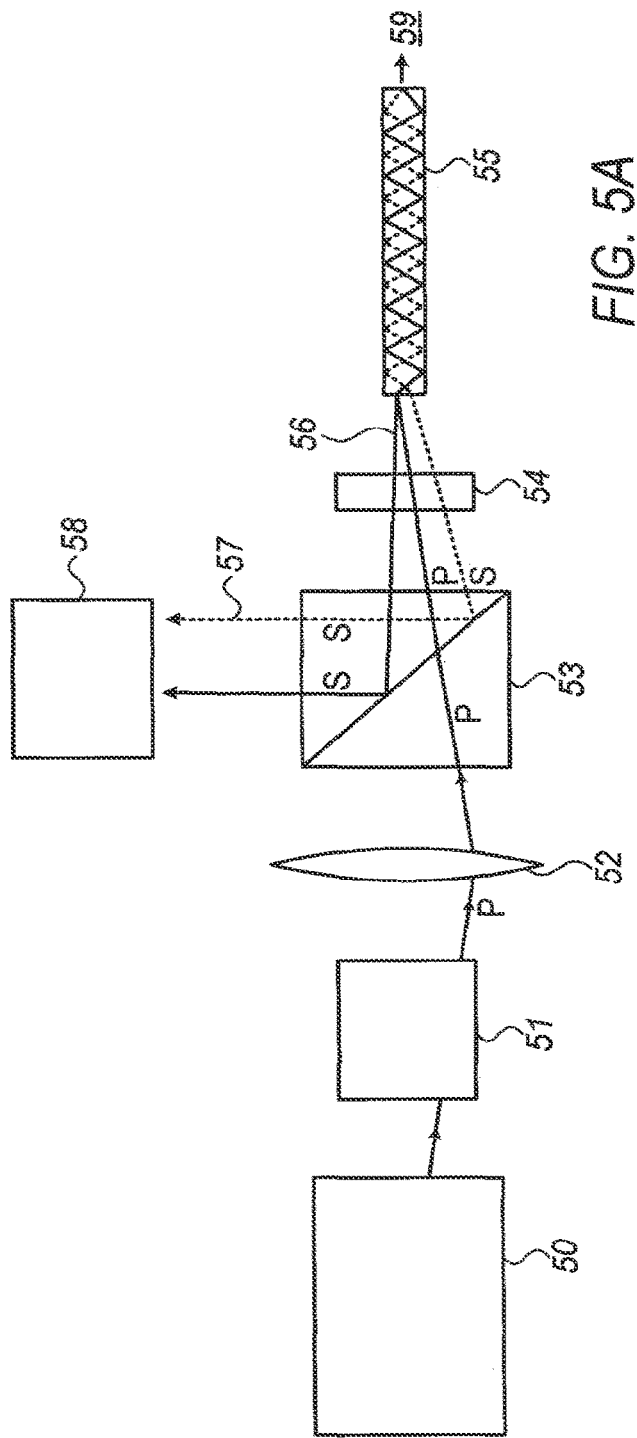
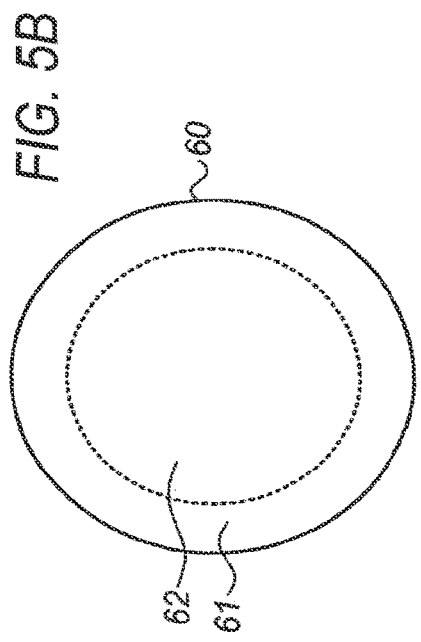
FIG. 5A
FIG. 5B

SYSTEM FOR TISSUE ABLATION USING PULSED LASER

CROSS-REFERENCE TO RELATED APPLICATIONS

This application is a continuation of, claims the benefit of and priority to, previously riled U.S. patent application Ser. No. 15/309,193 filed on Nov. 6, 2016, which is a national phase of International Patent Application No. PCT/IL2015/050529 filed May 18, 2015, which claims priority to U.S. Provisional Patent Application No. 61/994,904 filed on May 18, 2014 and U.S. Provisional Patent Application No. 62/006,389 filed on Jun. 2, 2014. The disclosures of each of the aforementioned international, non-provisional, and provisional patent applications are hereby incorporated by reference in their entireties.

FIELD OF THE INVENTION

The present invention relates to the field of pulsed high power lasers and the problem of delivering their output through optical fibers and especially for use in tissue ablation with the energy transmitted through those fibers.

BACKGROUND OF THE INVENTION

Delivery of high pulsed laser power through optical fibers is widely used for ablation of tissue or other targets. For such ablation procedures, ultra-violet (UV) light has many advantages, as it is well absorbed by biological matter and organic compounds. Rather than burning or cutting material, the UV laser adds enough energy to disrupt the molecular bonds of the surface tissue, which effectively disintegrates into the air in a tightly controlled manner through ablation rather than burning. The laser energy is also strongly absorbed and leads to sharp local elevation of temperature and results in generation of strong mechanical forces leading to photo-acoustic and photo-thermal ablation. Thus lasers emitting in the ultraviolet have the useful property that they can remove exceptionally fine layers of surface material with almost no heating or change to the remainder of the surrounding material which is left intact. Excimer lasers emitting at 308 nm (XeCl) are commonly used. However, such lasers are bulky, require careful maintenance and frequent calibration, and the beam quality is poor and may not be stable. Third harmonic, Q-switched Nd:YAG lasers emitting at 355 nm have also been used for such UV ablation procedures.

In order to obtain effective tissue ablation, fluencies above a certain threshold are required, and high peak power pulses, of the order of 50 mJ/mm$^2$ in pulses of down to the 10 nsec range are generally desired. The delivery of such fluences is very challenging for the optical fibers, and can lead to damage at the entrance or exit facets of the fiber, or in the bulk of the fiber by selective heating, plasma generation, self-focusing or the generation of cracks at the exit facet. In order to overcome the challenge of this kind of damage, methods have been proposed in the prior an of taking the high quality beam emitting by the laser, and of homogenizing the beam before input to the fiber, to eliminate "hot spots". Some such methods that have been proposed include:

(i) The laser is coupled to the optical fiber using a diffractive optical element (DOE) and a coupling lens. The DOE homogenizes the beam spatial energy density and eliminates "hot spots" of the laser. The DOE can form different shapes, including a square, a circle, rectangular, as adapted to the different shapes of the input plane of a bundle of fibers. Different coupling lenses and different distances between the DOE and the coupling lens have been used, in order to obtain different spot sizes.

(ii) A micro-lens array is used to achieve a homogenized spot. More than one array can also be used in order to achieve better homogeneity and to avoid hot spots due to beamlet interference. The size and shape of the spot can be manipulated by varying the pitch size and the coupling lens focal length. Such a micro-lens array homogenizer for executing the coupling of high peak power laser pulses into optical fibers, has been described in an article by T. Schmidt-Uhlig et al, entitled "New Simplified Coupling Scheme for the Delivery of 20 MW Nd:YAG Laser Pulses by Large Core Optical Fibers", published in Applied Physics B, Lasers and Optics, Vol. 72, pages 183-186 (2001).

(iii) Use of a multimode fiber in order to homogenize the beam energy density. A positive lens is used to couple the laser beam into the homogenizer fiber, and a second positive lens is used to image the homogenizer fiber output into the fiber delivering the beam to the ablation target. A convenient option is to use a fused silica fiber, which is more suitable for high power transmission.

(iv) The use of pairs of pulses to achieve effective removal of tissue from a surgical site, in which the first pulse "conditions" the tissue which can then be more easily removed by a second, often longer pulse. This arrangement enables ablation to the accomplished with less damage to the fiber than if an equivalent single pulse were to be used. Such a method is described in U.S. Pat. No. 5,312,396 for "Pulsed Laser System for the Surgical Removal of Tissue" to M. S. Feld et al.

Additionally, a similar procedure using multiple pulses is described in the article by D. Albagli et al entitled "Time dependence of laser-induced surface breakdown in fused silica at 355 nm in the nanosecond regime", published in SPIE Vo. 1441, Laser induced Damage in Optical Materials, 1990. Using first and second pulses of the pair at two different wavelengths may also be advantageously used.

In an alternative approach, the pulse length of the laser has been extended to more than 100 nsec in order to improve the damage threshold of the fibers, or has been split into at least two pulses with a 100 to 200 nsec delay between them, but this comes at the expense of the ablation efficiency of hard tissues, such us highly calcified lesions as described in the article by Rod S. Taylor et al entitled "Dependence of the XeCl laser cut rate of plaque on the degree of calcification, laser fluence, and optical pulse duration" published in "Lasers in Surgery and Medicine" Volume 10, Issue 5, pages 414-419, 1990.

However, all of the above mentioned methods have disadvantages, particularly in terms of the limited improvement in energy density carrying capacity that can be achieved for the optical fiber setup used, and/or the system energy throughput, and/or damage to the fiber tip when in contact with tissue.

There therefore exists a need for a method and apparatus for performing ablative surgical methods using fiber optical delivery of the ablation energy, which overcomes at least some of the disadvantages of prior art systems and methods.

In addition to the need for new systems for enabling the ablation process, there is a growing need for the specific procedure of removing pacemaker and defibrillator leads in patients, due to such reasons as lead fracture or abrasion of the insulation causing shorting and infections. Approximately 5 million leads are implanted worldwide and it is estimated that 4-7% will have to be removed at some time during the patient's lifetime. It is estimated that over 100,000 leads were extracted in the US and Europe in 2010.

In Lead Extraction procedures, known hereinafter as LE, the most critical point in the procedure is reached when the lead at a bend in the vein has to be debulked. When the electrode separation procedure is performed, there is a risk of perforation of the vein by the catheter, and in severe cases, this can even result in death of the patient. Rates of 1% death cases or even higher are reported using active dilators.

Laser ablation and mechanical based cutters are widely used solutions for atherectomy procedures in order to open or partially open blockages inside blood vessels. One of the methods of reducing the danger of the vessel wall perforation is by using a system having parameters which preferentially cut or ablate the atheroma tissue over the wall of the blood vessel. If the cutting or ablating effect is significantly more effective on the atheroma material than on the artery or vein wall material, and the procedure is executed under conditions which fall safely below the threshold at which damage may be caused to the vessel wall, there will be less likelihood that the artery or vein wall will be cut during the debulking procedure. In the prior art, in an article entitled "Preferential Light Absorption in Atheromas in Vitro—Implications For Laser Angioplasty" by M. R. Prince et al, published in Journal of Clinical Investigation Vol. 78(1): pages 295-302, July 1986, it has been shown that atheromas indeed absorb more than the normal aorta between 420 and 530 nm. However, this was not found to be so in the UV, where at the widely used 308 nm wavelength, the absorption by the aorta is higher than that of atheroma. However, since use of the 420-530 nm range, with its advantageous ablation selectivity, has an inherent disadvantage in the potential thermal damage caused by the larger energies needed for efficient ablation and deeper penetration, it is preferable to use a method for selective ablation which uses laser radiation within the UV region.

However, it has also been found, as described in the article entitled "Laser Ablation of Atherosclerotic Blood Vessel Tissue Under Various Irradiation Conditions" by R. O Esenaliev et al, published in IEEE Transactions on Biomedical Engineering. Vol. 36, no. 12. Pages 1188 to 1194 (December 1989), that for wavelengths in the UV (355 nm and 266 nm), no difference in the optical attenuation coefficients to short pulses, has been found between the normal wall and fibrous plaque areas of atherosclerotic blood vessels. Therefore, other prior art methods, such as shown in the article entitled "Selective Absorption of Ultraviolet Laser Energy by Human Atherosclerotic Plaque Treated with Tetracycline" by D. Murphy-Chutorian et al, published in the American Journal of Cardiology, Vol. 55, pages 1293-1297, 1985, have suggested the use of sensitizers such as tetracycline, to increase the absorption in the plaque. Tetracycline binds strongly to the plaque and has strong absorption in the UV. The problem with such methods for use in clinical treatments is that tetracycline is an antibiotic, and needs additional regulation and tests to ensure absence of side effects.

There therefore also exists a need for a method and apparatus for safely performing lead extraction, using fiber optical delivery of the ablation energy, which overcomes at least some of the disadvantages of prior art systems and methods. Similarly, there is a need for atherectomy tools for debulking of atheroma in blood vessels that reduce the risk of vessel perforation or dissection and debulking of enlarged glands in Benign Prostatic Hyperplasia (BPH) while reducing the risk of capsule injury.

Laser catheters should be calibrated prior to the operation in order to verify the fluence and the repetition rate of the laser energy that is emitted from the catheters.

The prior art deals with methods of calibration of catheters in which the catheter is pulled out of its packaging, coupled to the laser system, the distal tip is held by a housing in front of a detector, the laser is operated and the energy is measured by the detector as described in U.S. patent Ser. No. 11/946,376 for "Laser catheter calibrator" to Tom Dadisman.

Since the catheters are sterilized before use, this method can involve risk of moving the distal tip of the catheter out of the sterilized area in the operation room.

There therefore also exists a need for a method and apparatus for internal calibration of the laser system and for detecting a failure of the system and/or the catheter.

The disclosures of each of the publications mentioned in this section and in other sections of the specification, are hereby incorporated by reference, each in its entirety.

SUMMARY

The present disclosure describes new exemplary systems for enabling the coupling and transmission of very high energy pulses having a very short pulse width, preferably from a solid state Q Switched laser emitting in UV, into optical fibers for use in ablation procedures, which enable substantially higher energy pulses to be transmitted than in the systems described in the prior art. In prior art systems, a laser having as high a quality output as possible is generally used, in keeping with the mantra that in order to achieve high coupling efficiency and better beam quality without "hot spots", a laser having the mode closest to a single mode output should be used, generally as close as possible to a diffraction limited. Gaussian mode. This is the accepted logic in the use of laser beams for cutting or spot ablation, as indicated for instance in the above-mentioned U.S. Pat. No. 5,312,396, where it is stated, in extolling their suitability for the purpose, that the Nd:YAG lasers used "have good beam quality". Similarly, in the above referenced article by T. Schmidt-Uhlig et al, it is stated that the pulses of the Q-switched frequency doubled Nd:YAG laser used in their system had "a nearly gaussian (sic) temporal and spatial profile". The same design philosophy applies through most of the prior art high pulse energy, fiber-delivered surgical ablation systems. Similarly, the article by B. Richou et al entitled "Delivery of 10-MW Nd:YAG laser pulses by large-core optical fibers: dependence of the laser-intensity profile on beam propagation" published in Applied Optics Vol. 36, No. 7 (1997), reported higher (230 mJ) transmission of a pulsed Nd:YAG near-Gaussian beam compared to a flat-hat beam (130 mJ). The individual fibers used in the fiber bundles of the systems of the present application generally have core diameters of less than 200 microns, and preferably less than 100 microns, wherein the energy transmitted is in the order of 1-2 mJ with pulse length of 10 ns cannot lead to self-focusing.

However, the system design used in the present application, uses the fact that it is precisely because of the high quality mode structure of such lasers that the serious problems of coupling and transmission through the optical fiber arise, even when dealing with fibers with small diameter such as 100 micron core fibers.

The presently described system differs from these prior art systems in that a source laser outputting multiple transverse modes is used, thereby having a highly multimode output.

The cavity should also advantageously be a stable resonator cavity. Such a laser a priori outputs a beam with low spatial coherence, and therefore reduces the prevalence to damage in the bulk of the fiber due to interference phenomena. Such a laser outputs a beam which is significantly closer to having a uniform beam profile, known as a top-hat configuration, than the prior art, high quality lasers generally used in such systems. In order to improve the immunity from fiber damage even more, prior art homogenization, beam manipulation methods can also advantageously be applied to such a flat-topped beam, with accordingly improved performance. The transmission of such pulses down the fibers results in a higher damage threshold than when using high quality laser pulses, and it has been found possible to transmit pulses having higher energy density, than those of prior art systems, before fiber damage sets in. It is believed that this phenomenon is related to the absence of meaningful interaction between discrete parts of the beam across its profile, which could generate hot spots or interference. However, it is to be understood that the invention is claimed independently of the real reason for its physical operation. It should be noted that since the catheters of the present disclosure utilize a bundle of fibers, and the energy of the individual laser pulses is transmitted through a bundle of fibers and not a single fiber, references to single fibers within this disclosure is generally intended to mean a single fiber out of the bundle of fibers, and is not intended to mean transmission through solely a single fiber.

The mode quality of a laser output beam can be characterized by the beam size and beam divergence. The smaller the divergence for a beam of given size and wavelength, the higher the beam quality. One parameter used for characterizing the beam mode quality is the $M^2$ parameter. The $M^2$ parameter of the beam mode output by the laser is used in the present application to characterize the beam properties for achievement of very high pulse energy densities for such pulses in the nanosecond range. It is to be understood however that use of the $M^2$ parameter is only one way of characterizing beam quality, and the invention of the present disclosure is not intended to be limited by use of this measure.

The $M_2$ parameter is related to the ratio of the output beam size and the beam divergence by the following relationship:

$$M^2 = \frac{D\theta\pi}{4\lambda}$$

where D=the beam diameter,
λ=the wavelength of the laser beam, and
θ=the full angle beam divergence in radians.

A pure diffraction-limited beam would have an $M^2$ parameter of 1, while practical, high-efficiency, commercial lasers for use in surgical or precision industrial applications generally have an $M^2$ parameter in the low single digit range.

The $M^2$ parameter can also be defined for a beam at any point along its optical path, by inserting a focusing lens at that point and measuring the size of the focal spot obtained. Intuitively, the tighter the focal spot, the better the mode quality of the beam at that point, and the lower the $M^2$ parameter. The $M^2$ parameter in that case is given by the following relationship:

$$M^2 = \frac{Dd\pi}{4f\lambda}$$

where D is now the beam diameter at the point of insertion of the lens.
f is the focal length of the lens used, and
d is the size of the focal spot obtained.

It is to be understood throughout this disclosure that the $M^2$ parameter used is calculated according to the appropriate one of these formula, depending on whether the measurement relates to the laser output beam, or to a beam downstream in the optical path.

The systems and methods described in the present disclosure differ from those described in the prior art in that the laser used for transmission down the fiber and for ablation at the treatment site is selected to have a highly multimode beam output, preferably a third harmonic Nd:YAG laser, such that the $M^2$ parameter of the output beam should be at least of the order of a few tens, typically at least 30, and optimally up to 70 or even more, such as greater than 100. The $M^2$ of the laser may be greater than 10, but the $M^2$ of the system, including the optics is greater than 70 and preferably more than 200. Such beams therefore behave in a very distinct manner from those described in the prior art, and allow transmission of pulses having pulse energy densities at least twice as much, and even more, than the pulses available from prior art ablation systems using high beam quality lasers. Additional optical means may be added, such as a micro-lens array, to further increase $M^2$ and to increase pulse energy density transmitted reliably for a large number of pulses through fibers typically with 100 micron core or less.

Details of typical performance of such systems are to be found hereinbelow in the Detailed Description section.

The present disclosure furthermore describes new exemplary systems for enabling selective removal of undesired tissue within a blood vessel, while minimizing the risk of damaging the blood vessel itself, based on the use of the ablative properties of short laser pulses of 320-400 nm laser wavelength, with selected parameters of the mechanical walls of the tubes constituting the catheter, of the laser fluence and of the force that is applied by the catheter on the tissues. As stated hereinabove. It was previously believed that the selectivity characteristics of a given tissue without the existence of sensitizers could not be determined using UV radiation, since normal aorta and atheromatous tissues share numerous common molecules whose absorption bands are all in the UV region, whether at 355 nm or at 308 nm. Although the dissociation energy of many organic molecular bonds is typically higher than the photon energy of the 355 nm wavelength (3.5 eV), this does not apply to the 308 nm excimer laser wavelength, whose photon energy is higher (4 eV). Thus, it is believed that the dominant ablation mechanisms at the 355 nm wavelength is photomechanical. In contrast, at the shorter, 308 nm wavelength of the excimer laser, and obviously at even shorter wavelengths, photochemical processes, in which chemical bonds are dissociated by the laser radiation, are more relevant. Because of this difference in the interaction mechanism with the target tissue, this selection of wavelength, together with the other selected parameters, is believed to have a central influence on the success of the presently described catheters. Thus, by using the correctly selected parameters, ablation of the blood vessel walls is far less likely to occur than for the atheroma, because the blood vessel walls have greater elasticity than the atheroma, and therefore withstand the photomechanical mechanisms operating on them much better than the atheroma, which is more readily broken up by such photomechanical influences.

It is also possible that in addition to the operated wavelength aspects, since shock waves plays a major role in the photomechanical ablation mechanism, a reduction in the pulse duration (i.e. higher peak power) may lead to an increased efficiency of the process.

However it is to be emphasized that the present application relates to the catheters described therein, regardless of the physical mechanisms on which the success of their operation is based, and the application is not intended to be limited by any proposals regarding possible mechanisms by which the catheters fulfill their function.

According to one exemplary catheter system of the present disclosure, a third harmonic Nd:YAG laser outputting at 355 nm is coupled to a hybrid catheter, which incorporates a bundle of optical fibers receiving the laser illumination, and at least one blunt-ended tubular structure whose distal edge is located on an essentially single surface with the output facets of the optical fibers, to interact with the atheromatous tissue within the blood vessel. Different configurations am available for LE use and for debulking or opening blood vessels where substantial deposits of atheromatous material is found such as in Peripheral Artery Disease (PAD). In the LE case, a thin annular bundle of fibers is required, with cylindrical walls bounding it on the inner and outer sides of the annulus. The cylindrical walls constitute the blunt-ended tubular structure. On the other hand, in PAD, for removal of deposits across the whole cross-section of a blood vessel, the bundle of fibers essentially covers the whole of the cross section of the catheter, usually with a thin opening in the center of the bundle for a guide wire, but in this case too, the cylindrical walls of the bundle region constitute the blunt ended tubular structure. Throughout this disclosure, these blunt ended tubular structures are termed "blunt mechanical blades".

Using the LE case as an example, the catheter operates, once within the blood vessel and in contact with the intravascular deposit, by using the laser pulses to ablate a thin layer of the tissue, typically only a few tens of microns deep, making a thin, shallow slit to enable the continued penetration of the blunt mechanical blade in response to the pressure applied distally on the catheter. The blade or blades are therefore constructed to be too blunt to initiate dissection, but with enough of an edge to create the slit to enable deeper catheter penetration into the tissue. The borders of the tissue being ablated, which possesses a transient zone, are mechanically weakened due to the trauma, which facilitates dissection by the blunt blade. The width of the blades, and the ratio of the total area of the cores of the fibers within the fiber optical bundle, from which the ablation energy is emitted, relative to the total cross-sectional area of the tip of the catheter, not including the empty central area, are important parameters which also characterize the catheters of the present disclosure.

The force applied distally on the catheter is an additional parameter whose level is adjusted to ensure that the catheter advances through the atheromatous tissue at a rate commensurate with the rate of laser ablation and mechanical peeling of the hybrid catheter action. The larger the diameter of the catheter, the larger the force that needs to be applied.

The present disclosure furthermore describes new exemplary systems to enable reliable operation of the catheter in a mode of contact with the tissue.

In some embodiments a thin sapphire window or similar is added at the distal end of the fibers. In some embodiments the window is coated with an AR coating.

In other embodiments, the fiber ends at the distal tip are coated with a hard coating. Coating the catheter tip may provide additional performance enhancement. One possible material is diamond. Diamond Like Coatings (DLC) are commonly used in industrial applications where hard, strong, and smooth surfaces are required, for example, to protect from mechanical wear. One of the means to obtain such coatings is through Chemical Vapor Deposition (CVD). Cutting tools are often coated to improve durability. DLC has excellent biocompatibility as it is commonly employed in joint replacements and coronary artery stents.

A diamond coated catheter may have the following advantages. First, the coating hardness may protect the fiber tips from damage due to contact with hard biological media and from the resulting shockwaves from laser ablation. Second, the smoothness (low friction) and simultaneous nano-roughness may be advantageous to allow progression of the catheter and/or enhanced material removal by scraping. Third, the high thermal conductivity may help to distribute heat from absorption of the laser pulses in the tissue.

DLC's are generally not thought suitable for visible wavelengths due to their high absorption. However, when considering the optimal layer thickness required for maximum UV light (355 nm) transmission, a DLC coating with an index of 2.4 would only need to be about 74 nm thick when applied to fused silica in order to obtain a minimum reflection of 3.7%. Absorption of the material should be minimal with such a low thickness. Furthermore, transparent diamond coating can used such as described in the article of E. Pace et al entitled: "Fast stable visible-blind and highly sensitive CVD diamond UV photodetectors for laboratory and space applications" published in "Diamond and Related Materials", Volume 9, Issues 3-6, Pages 987-993 (April-May 2000). Several manufacturers have applied DLC coatings to glass, including, for example, Jenoptik and Reynard Corporation which produces Clear DLC with enhanced visible light transmission.

Another limitation of use of CLD is the high index of refraction which leads to very high "Fresnel Loses". A potential way to deal with those loses is to add an AR coating, but this is problematic in the current embodiment due to a number of reasons:

The AR coating can't withstand very high power at the fiber tip. In addition, it needs to be made from biocompatible materials to allow close contact with tissue. Furthermore, the AR coating is subject to mechanical abrasion when in contact with tissue.

Thus, according to the present invention, a diamond layer is used as an AR film wherein its thickness is selected to reduce reflection loses in order to save energy and avoid back reflection into the fiber that can damage it. The thickness can be determined according to the rules used in antireflection coatings such as quarter wavelength, 5/4 wavelength or other combinations according to the angle of emitted light (NA). The thickness can also be determined in such a way that a 355 nm wavelength will be transmitted while another wavelength in the visible are will be reflected. For example, the hard coating at the exit facet can be such that transmits the 355 nm out of the catheter by using a thickness of 9/4 wavelength wherein the wavelength is 355 nm (and corrected according to the refraction index) so that the same layer will be 3/2 of the wavelength at 532 nm (and corrected according to the refraction index) and result in effective back reflection from the fiber end facet for calibration of energy delivered by the system, wherein the 532 nm and 355 nm are generated by the same laser and transmitted through the same coupling optics and catheter. This enables effective calibration before the procedure and serve as on-line calibration and quality control of the catheter throughout the procedure. By mode of example, if the index of refraction is 2.4, a layer with the thickness of 332.8 nm is equivalent to 9/4 wavelengths of 355 nm (in vacuum) and to 1.5 wavelengths of 532 nm (in vacuum). Other embodiments are possible that are optimized for the incident of laser rays transmitted through the fiber that can get up NA of 0.22.

In other implementations, the laser pulse is split into at least two pulses with a delay between pulses of less than 15 nsec delay in order to protect the distal facets of the fibers without significant impact on ablation efficiency. Details of such system can be found below in the detailed description section.

In alternative implementations means to facilitate the flushing of the tip with saline throughout the procedure are described. Details of typical performance of such systems are to be found hereinbelow in the Detailed Description section.

The present disclosure furthermore describes new exemplary systems to enable effective and convenient apparatus for calibration of laser system delivering energy through the fibers. Details of typical performance of such systems are to be found hereinbelow in the Detailed Description section.

There is thus provided in accordance with an exemplary implementation of the devices described in this disclosure, a laser device for ablating a region within a luminar vessel, comprising a pulsed laser, and at least one optical fiber coupled to said laser by means of a coupling optic, wherein the laser has a multimode output such that its $M^2$ parameter is larger than 30. The $M^2$ parameter may be larger than 70 or even 100.

According to another implementation of such devices, there is provided a laser device for ablating a region within a luminar vessel, or other lumens in the body, comprising a pulsed laser emitting in the ultra violet region of the spectrum, and at least one optical fiber coupled to said laser by means of a coupling optic, wherein the laser beam has a multimode profile as measured by the spot size of the beam focused by a lens of known focal length, such that the beam has an $M^2$ parameter of at least 30. The $M^2$ parameter may be larger than 70 or even 100.

In either of these two implementations, the at least one optical fiber may have a core of less than 200 microns diameter. Additionally, the coupling optics may comprise any one or more of a micro lens array, a diffractive optical element, a holographic diffuser, a light pipe rod, and a large core optical fiber. In some implementations, $M^2$ parameter of the laser may be larger than 10 or alternatively greater than 30 but the $M^2$ of the laser together with the above mentioned elements is larger than 70 and preferably greater than 200.

The pulsed laser may advantageously be a Nd:YAG, solid state laser, the laser wavelength may be 355 nm, the laser pulse width may be less than 15 nsec and the pulse laser repetition rate may be greater than 10 Hz. In the latter case, the laser is such that a fluence of at least 60 mJ/mm$^2$ can be delivered through the optical fiber for more than one minute. According to further implementations, the fluence delivered through the optical fiber for more than one minute may be at least 200 mJ/mm$^2$ or even 300 mJ/mm$^2$.

There is thus provided in accordance with an exemplary implementation of the devices described in this disclosure, a device for selective cutting within blood vessels, wherein the device comprises:
(i) a pulsed laser emitting in the wavelength range of 320 to 400 nm, and being coupled to a plurality of optical fibers, such that a flux of energy is emitted from the fibers, and
(ii) tubes acting as boundaries to the plurality of fibers, each of the tubes having a blunt distal edge in the same axial plane as the output end of the plurality of fibers, such that when a distal force is applied to the device, the blunt distal edges push through atheromatous material in the blood vessel in the region where the flux of energy is emitted from the fibers,
wherein the ratio of the total core area from which the flux of energy is emitted to the total distal tip area of the device is at least 25%.

In such a device, the ratio may be in the range of 30% to 40%. Additionally, the laser may advantageously be a third harmonic Nd:YAG laser emitting at 355 nm.

In any of the above described devices, the flux may be at least 50 mJ/mm$^2$ or it may be in the range of 50 to 80 mJ/mm$^2$, or even in the range of 65 to 80 mJ/mm$^2$.

Additionally, the plurality of fibers of the above described device may be a bundle of fibers. In such a case, the overall width of each of the tubes and the fibers should be less than 400 μm and more than 200 μm.

Furthermore, according to yet more implementations of such devices, dyes or substrates may be used to enhance absorption at desired wavelengths. The dye may be tetracycline and the desired wavelength 355 nm.

Another example implementation can involve a system for ablating a region of a tissue, comprising:
(i) a laser emitting a beam of laser pulses, the beam being coupled by means of coupling optics to at least one optical fiber, such that a flux of energy is emitted from the at least one fiber, the at least one fiber having an input facet and an output facet,
(ii) a beam splitter disposed between the laser and the at least one fiber, such that the beam can pass undeflected through the beam polarizer to the at least one fiber, for transmission to the region of tissue, and
(iii) a detector disposed at the beam splitter in a position normal to the direction at which the beam passed undeflected through the beam splitter,
wherein the detector receives a predetermined fraction of the beam reflected from at least one of the input facet and the output facet of the at least one optical fiber, such that the flux of energy passing through the at least one optical fiber can be determined.

Such a system may further comprise
(i) a linear polarizer disposed in the optical path of the beam, such that the beam has a predetermined linear polarization before impinging on the beam splitter, and
(ii) a quarter wave plate disposed between the beam splitter and the input facet of the at least one fiber, such that the predetermined fraction of the beam reflected from at least one of the input facets and the output facets has a linear polarization orthogonal to that of the beam inputting the at least one fiber, such that the beam splitter directs the predetermined fraction towards the detector.

In either of the latter two cases, one of the input and output facets may have an anti-reflective coating, such that the predetermined fraction of the reflected beam is limited to that facet which is uncoated.

BRIEF DESCRIPTION OF THE DRAWINGS

The present invention will be understood and appreciated more fully from the following detailed description, taken in conjunction with the drawings in which:

FIG. 5A illustrates schematically an arrangement for calibrating the hybrid catheters described in FIGS. 1 to 4B during their operation, and to detect malfunction of the system in real time.

FIG. 5B illustrates schematically end view of exemplary spatial filter for the calibration system described in FIG. 5A.

DETAILED DESCRIPTION

Figure 1:
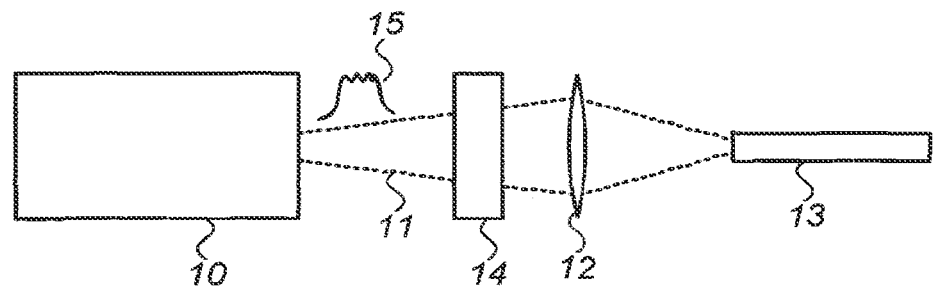
FIG. 1 illustrates schematically an exemplary laser ablation system using a multimode laser, which enables the transmission of very high energy density pulses through optical fibers of an ablation catheter.

Reference is now made to FIG. 1, which illustrates schematically an exemplary laser ablation system, of the type described in the present disclosure, incorporating a solid state laser source 10 emitting in the ultra-violet, and having a multi-mode output, as exemplified by the beam profile representation 15 adjacent to the output beam. The representation is only for illustrative purposes to show the multi-mode output as being very distant from a Gaussian beam, and is not intended to limit the application in any way. The laser beam output should have an $M^2$ parameter of at least 30, and more advantageously at least 70, though lasers having a beam output with an $M^2$ parameter of over 100 can provide even better performance in the exemplary ablation system of FIG. 1. For optimum performance, short pulse widths are used, preferably less than 10 nanoseconds, and the laser should supply pulses that can provide an energy density of at least 50 $mJ/mm^2$ through the fiber. For stability and compactness, a solid state laser is used, such as a Nd:YAG, operating at its third harmonic 355 nm.

Although the laser 10 emits a well-mixed multimode beam, the laser beam is input to a beam homogenizing and/or coherence manipulation unit 14, in order to mix the multiple modes of the output beam 11 even more, such that the fiber has an even higher damage threshold than would be obtained with the multimode output from the laser alone. This unit 14 can be any one or more of a homogenizing plate, a diffractive optical element, a holographic element, a micro-lens array, or a homogenizer optical fiber bent to ensure additional mode mixing during propagation of the pulses down it. A coupling lens 12 is then used for coupling the laser beam into the optical fiber bundle 13. Although the individual fibers could have a core size of less than 200 microns, the optical fiber bundle includes a large number of these individual fibers, and is thus substantially larger than the diameter of the individual fibers, such that there are no special optical difficulty in coupling such a multimode beam into such small fibers. Although only one coupling lens 12 is shown in FIG. 1, it is to be understood that the system could incorporate two coupling lenses—one to couple the raw laser beam into a homogenizer fiber, for instance, and the other to couple the output of the treated beam into the fiber bundle of the catheter. In some embodiments combination of such optical elements enable delivery of high fluencies through fibers of 100 micron or less a laser beam with $M^2$ greater than 10 may also be used.

Figure 2:
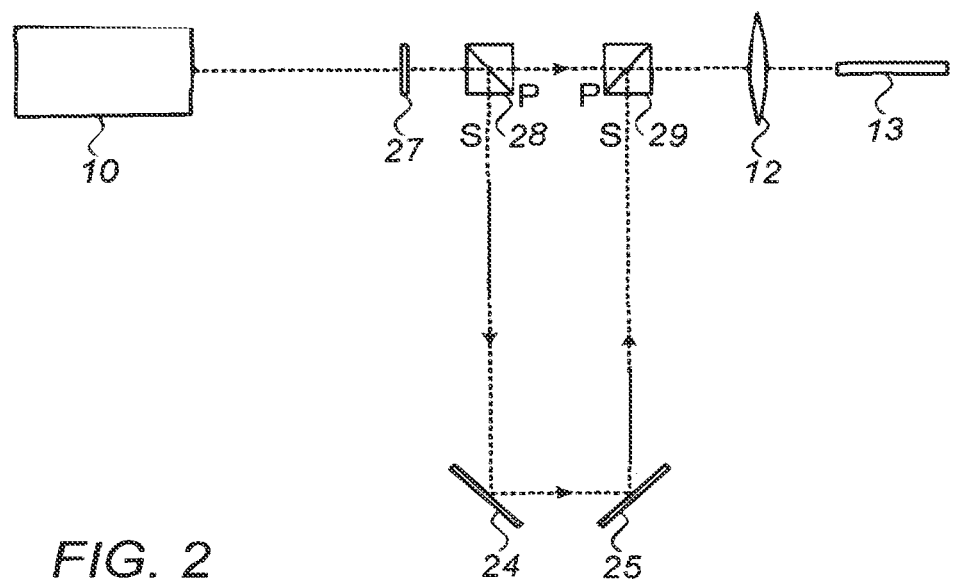
FIG. 2 illustrates schematically a further exemplary implementation of the system shown in FIG. 1, in which splitting of the laser beam is used in order to enable transmission of the pulse train through the fiber in the form of double pulses temporally separated and avoid damage at the output facets of the optical fibers.

Reference is now made to FIG. 2, which illustrates schematically a further exemplary implementation of the system shown in FIG. 1, in which polarization splitting of the laser beam is used in order to enable transmission of the pulse train down the fiber in the form of double pulses temporally separated, particularly reducing the danger of damage to the output facet of each of the fibers when in contact with tissue. These output facets, where the fibers are in contact with the tissue being ablated, are subject to particularly harsh conditions. When the system described in FIG. 1 is implemented and the fibers are in contact with tissue the likelihood of facet damage is greater at the output facets than at the input facets of the fibers, and therefore this implementation will be most effective to protect the output facets from damage, it is to be understood that it is also useful for protecting both the input facet, and the fiber bulk itself.

The beam from the highly multimode laser 10, is transmitted through a half wave plate 27 and then to a polarization beam splitter 28 in order to split the laser beam into two component parts—S-polarized and P-polarized. In the example shown in FIG. 2, the S-polarization is deflected through 90.degree, while the P-polarization passes through the cubic beam splitter without deflection. The S polarization is conveyed on an optical path longer than that of the P polarization, and after reflection through 180.degree, accomplished by means of two full reflector mirrors, the S- and the P-polarization beams are recombined by means of a second polarization beam splitter 29, ready for coupling by means of the coupling lens 12 into the fibers 13 of the catheter. By adjusting the optical path difference along which the P- and S-polarizations travel, it is possible to control the temporal delay between the two beams, such that the input is made up of double pulses, separated by the selected time delay, and the use of such a double pulse laser energy enables the avoidance of fiber damage, not only at the entrance facet of the optical fiber, but also on the problematic output facet of the optical fiber, in contact mode with the ablated material. The time delay has to be selected such that the double pulses are not separated by more than the relaxation time of the vascular material being treated, such that ablating efficiency is not lost. For 10 ns pulses, a time delay between pulses of the order of 10 ns is regarded as being acceptable. The success of this double pulse mode depends also on the knowledge that the ablation efficiency is not a linear function of peak power of the laser pulse, such that division of the power into two pulses does not degrade the ablation effect by the same factor of two. Additionally, a lens (not shown in FIG. 2) could be disposed in the longer optical paths in order to image the beam waist in such a manner that the waists of the two beams traversing the two different optical paths are both located at the fiber input facet. This is necessary in order to compensate for the extra beam divergence which the beam in the longer optical path undergoes. As an alternative to the configuration shown in FIG. 2, it is possible to use thin film polarizers (TFP) to split and combine the two beams.

Furthermore, the laser beam may split into more than two channels, to even further reduce the potential damage level of the fibers. Additionally, different wavelengths emitted by a laser, such as the second and third harmonics, or the fundamental and third harmonic of the Nd:YAG laser, can be split and combined again. It is also possible to use multiple lasers with a synchronized delay between the pulses.

Figure 3A:
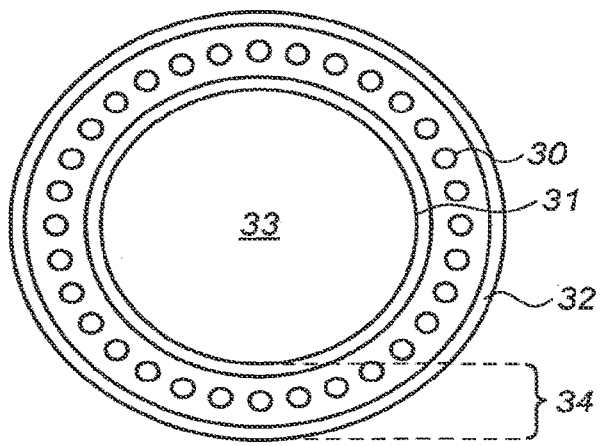
FIGS. 3A and 3B are respectively a schematic end view and a cross sectional side view of an exemplary annular hybrid catheter which can selectively ablate atheromatous tissue over the tissue of the wall of blood vessels, such that lead extraction or PAD procedures can be more safely performed.
Figure 3B:
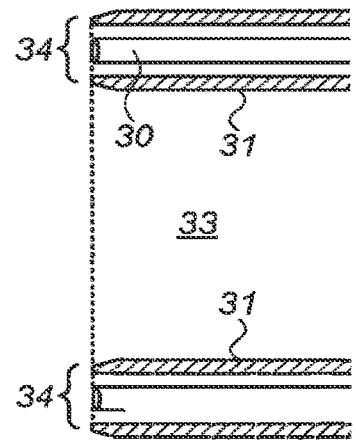
Figure 4A:
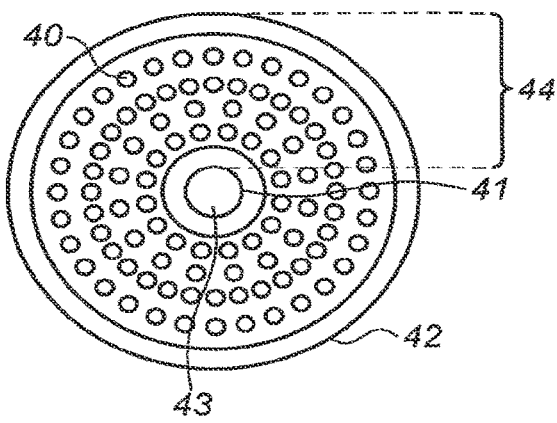
FIGS. 4A and 4B are respectively a schematic end view and a cross sectional side view of an exemplary hybrid catheter which can selectively ablate plaque from atherosclerotic blood vessels more safely.
Figure 4B:
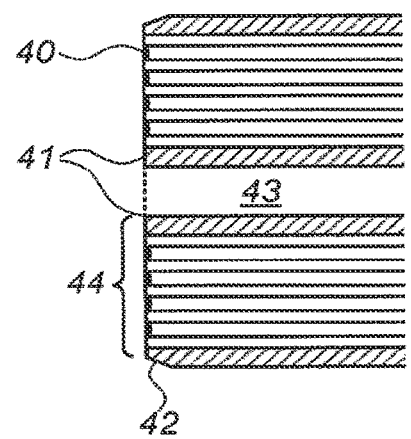

Reference is now made to FIGS. 3A and 3B and to FIGS. 4A and 4B which show schematically further implementations of hybrid ablation catheters of the present disclosure, which illustrate how the catheters can be used to selectively ablate atheromatous material from the blood vessels, while reducing the danger of perforating the blood vessel wall. The structures of the hybrid catheters shown in these drawings have the common feature that besides the fiber bundles emitting the ablating laser pulses, the blunt distal ends of the tubular elements enclosing the fiber bundles are also constructed such that they contribute to the operation of the catheters. As explained in the summary section of this disclosure, the distal ends of the tubular structures are specifically constructed having non-sharp ends, called hereinbelow blunt mechanical blades, so that they do not unintentionally dissect the blood vessel walls.

Referring first to FIGS. 3A and 3B, they show respectively a schematic end view and a cross sectional side view of an exemplary annular hybrid catheter which can selectively ablate atheromatous tissue substantially more readily than the walls of blood vessels, such that lead extraction can be more safely performed. The laser energy is transmitted to the distal end of the catheter through a bundle of optical fibers 30 embedded within an adhesive matrix, in the form of an annulus having a large central clear area 33. The annulus of optical fibers 30 is bounded on its inner side by a thin tube 31, which constitutes the inner blunt mechanical blade, and on its outer side by another thin tube 32, which constitutes the outer blunt mechanical blade. The distance between the innermost edge of the inner tube 31 and the outermost edge of the outer tube 32 is known as the effective wall thickness 34 of the catheter, or the distal tip. In use, the catheter is inserted into the blood vessel over the lead to be extracted, such that the lead is situated in the central annular area 33. The laser pulse energy is applied to the fiber bundle 30, typically in the ultraviolet region of 320 to 400 nm, and having a fluence of 50 to 80 mJ/nm2, accompanied by a force applied distally to the catheter, enables the catheter to proceed in a distal direction debulking the lead from the walls of the blood vessel, without damaging the walls of the blood vessel, as explained in the summary section hereinabove. The important parameter for the success of this process is based on the trade-off between two energetic processes taking place at the tissue interaction plane at the tip of the catheter. On the one hand, the total area of the fiber cores emitting the laser pulses, known as the active emitting area, is providing the ablating energy in order to degrade the atheromatous material, while the mechanical force exerted distally on the catheter, which pushes and peels off the degraded material mechanically, operates through what is termed the distal tip area, which includes all of the mechanical parts of the distal face of the catheter, including the inner and outer blunt mechanical blade areas, and the mechanical area of the fiber adhesive matrix, but not the hollow central area. The wall thickness or distal tip 34 of such catheters is typically in the range of 200 to 400 µm, such that the ratio of the fiber core area to the distal tip area of the catheter is between 25% and 50%. The most effective ratio is in the range of 30% to 40%. The distal force applied to the catheter may be in the region of 0.5 kg and even up to 2 kg.

FIGS. 4A and 4B now show in end view and in cross sectional side views, an exemplary hybrid catheter which can selectively ablate plaque from atherosclerotic blood vessels more safely, such as for use in PAD treatment. This type of catheter differs from that shown in FIGS. 3A and 3B in that the fiber optical bundle 40 fills the majority of the central region of the catheter, leaving only a small central opening 43 inside the inner tube 41, typically left so that the catheter can ride on a guide wire. The effective wall thickness 44 of this hybrid catheter is the distance between the outer surface of the outer tube 42 and the inner wall of the inner tube 41, and is typically in the range of 40 to 1,200 µm. As in the case of the LE catheter, the ratio of the fiber core area to the distal tip area of the catheter is between 25% and 50%. Because of the nature of the PAD treatment, more care is required in pushing the catheter through for instance a curved blood vessel, such that the force may be smaller, but at least 100 gm.

Reference is now made to FIG. 5A, which illustrates schematically an arrangement for calibrating the hybrid catheters described in this disclosure. Calibration is necessary prior to the operation in order to verify the fluence and the repetition rate of the laser energy that is emitted from the catheters.

In the prior art, methods of calibration of catheters have been described in which the catheter is coupled to the laser system, while the distal tip is held by a housing in front of a detector, and the transmitted energy is measured by the detector while the laser is operated. Since the catheters are sterilized before use, this method can involve the risk of moving the distal tip of the catheter out of the sterilized area in the operation room.

The system shown in FIG. 5A differs from prior art methods in that it enables the internal calibration of the catheter, while it is in use, and also enables detection of a failure of the system while it is operating.

The incident beam from the laser 50 is directed through a beam polarizer 51, which outputs the beam as P-polarized, as marked in FIG. 5A. After traversing the coupling lens 52, the P-polarized beam is input to a polarizing beam splitter 53, from which it emerges undeflected. The P-polarized beam is then input through a quarter wave plate 54, which converts its polarization to circular. This circularly polarized beam then enters the fiber 55, passing therethrough by total internal reflections (TIR), and the majority of the energy is emitted from the output facet at the distal end of the fiber, for use in the ablation procedure 59. However a small percentage of the energy is reflected back towards the entrance of the fiber due to Fresnel reflection from the output facet. Additionally, any Fresnel reflection 56 from the front facet is also reflected back. This small reflected fraction of the input beam now passes back through the quarter wave plate 54, where it is converted from circular into S-polarization, such that when it enters the polarizing beam splitter 53, it is deflected along a path 57 approximately normal to its entrance axis towards the detector 58. Since the percentage reflection from the front and rear facets is known, the detector is able to determine, from a measurement of this reflected power, the energy emitted from the fiber output to the ablation application. The measurement of the detector output is thus a real-time monitor of the laser energy being used in the ablation procedure.

If the entrance facet is coated with an anti-reflective coating, the power measured by the detector 58 is that due only to reflection from the output facet, such that differentiation can be made between reflections from these two facets.

An alternative to the use of an anti-reflective coating on the entrance facet in order to differentiate between the front and the rear facet reflections, it is possible to use a spatial filter disposed between the front facet and the polarizing beam splitter, in order to filter out the reflection from the input facet, which has a smaller divergence angle than the reflection from the output facet, since the numerical aperture of the output reflection is significantly larger. The spatial filter may conveniently be a thin film polarizer (TFP) as illustrated in FIG. 5B, wherein The TFP 60 is coated at its peripheral edges 61, such that those edges diverged the reflected beam from the output facet to the detector 58, while the central region 62 of the TFP 60 is uncoated and therefore the smaller divergence reflection from the input facet passes through that central uncoated window, and does not reach the detector.

According to another exemplary implementation, a cap may be placed over the distal tip of the catheter, with the inside of the cap is coated with reflective coating in order to enhance the signal that is reflected from the distal facets of the fibers.

The cap may be coated with a fluorescent material that changes the wavelength of the output reflected beam, and by use of an optical filter, its separation from the entrance facet reflection is achieved. The cap may be sterilized together with the catheter.

Alternatively, the cap may also be covered with material, polyamide for example, that gives a vocal indication when energy above specified level strikes it. Alternatively, the cup can be covered with material that changes it color when exposed to the radiation of the laser.

The above-described calibration procedure can be performed while the fiber is rolled up inside its packaging, keeping the bend radius of the fiber known and constant, so that the percent of energy reflected back from the output facet does not change.

In some other embodiments, the entrance facet is not coated, and the detector will measure both the energy reflected from the input and output facets.

In some embodiments, the system can be internally calibrated, without connecting the catheter, wherein there is a lid that is moved aside when the catheter is connected, and is closed when the catheter is moved out. This lid is mirror coated at the side that is pointing to the laser, and the energy reflected from this mirror coating is folded by the polarized beam splitter and can be measured in the detector.

The described method of calibrating such catheters also enables real time monitoring of the ablation process, by measuring the reflected energy in the system detector during the procedure and informing the user about energy degradation due to fiber damage.

Figure 6A:
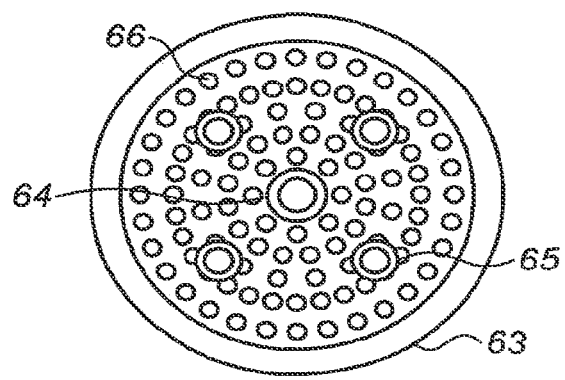
FIGS. 6A, 6B and 6C are respectively a schematic end view and a cross sectional side view of an exemplary catheters with capillaries for flushing the distal tip of the catheter.
Figure 6B:
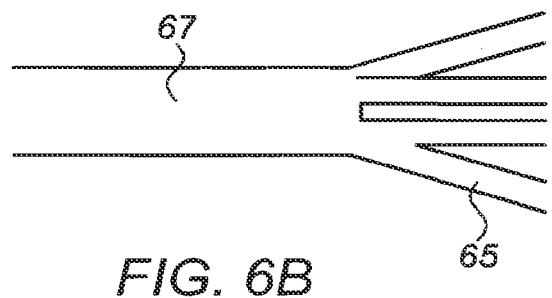
Figure 6C:
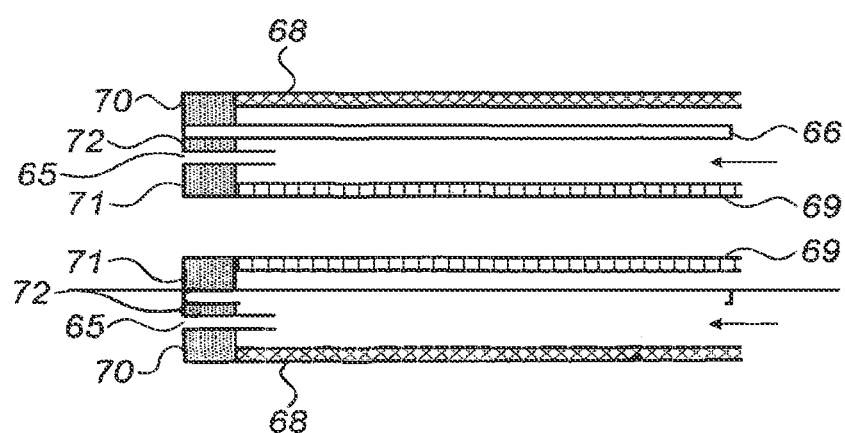

Reference is now made to FIGS. 6A to 6C. When UV laser catheters are used for debulking tissues inside the vessels, the distal tip of the fibers may be damaged due to the shock wave that is created because of the high absorption in the blood and in the contrast media. In order to protect the distal tip of the catheter, saline is injected through a guiding sheath in normal procedures. Alternatively, the saline can be injected through the inner lumen of the catheter, but this restricts the physician because of the need to choose smaller guidewire than possible.

Reference is now made to FIG. 6A wherein the distal end of laser catheter 63 is illustrated. Hollowed capillaries 65 may be incorporated between the optical fibers 66 and allow the flow of the saline to the point of contact of the distal tip of the catheter 63 and the ablated tissue. The hollowed capillaries 65 may extend from the handle to the distal tip of the catheter 63, and the saline is injected through the proximal side of the hollowed capillaries 65.

Reference is now made to FIG. 6B. In order to allow free flow of saline without the restriction of the capillaries forces, a large hollowed capillary 67 may be connected to the small and short hollowed capillaries 65 that are placed at the distal tip of the catheter 63. Another embodiment is illustrated in FIG. 6C. The Saline is injected in the space wherein the optical fibers 66 are located, between the inner tube 69 and the outer tube 68. The small capillaries 65 are located at the distal tip of the catheter, in between the glue 72, the inner blade 71 and the outer blade 70. Thus the capillaries 65 enable dripping of the Saline through the distal tip of the catheter.

While the present invention uses example from blood vessels, the utility is relevant for other medical indications requiring controlled resection of tissue such as Barrett's esophagus, flat polyps' removal in the intestine or in urology and gynecology applications such as debulking in BPH.

It is appreciated by persons skilled in the art that the present invention is not limited by what has been particularly shown and described hereinabove. Rather the scope of the present invention includes both combinations and sub-combinations of various features described hereinabove as well as variations and modifications thereto which would occur to a person of skill in the art upon reading the above description and which are not in the prior art.

What is claimed:

1. An optical system operable with a laser source for ablation of a target tissue, the optical system comprising:
   a plurality of optical elements arranged and configured to, when in optical communication with the laser source:
      receive a pulsed laser beam from the laser source, wherein the pulsed laser beam comprises a beam propagation ratio (M2) greater than or equal to 10; and
      form, based in part on the pulsed laser beam, a modified pulsed laser beam comprising:
         a pulse width less than or equal to 25 nanoseconds (ns), and
         a temporal delay between at least two component parts of the modified pulsed laser beam, the temporal delay equal to or less than a relaxation time of the target tissue.

2. The optical system of claim 1, wherein the plurality of optical elements includes a first polarizer configured to separate the received pulsed laser beam into a first polarized laser beam and a second polarized laser beam.

3. The optical system of claim 2, wherein the plurality of optical elements further includes at least one mirror arranged and configured to introduce the temporal delay into the second polarized laser beam.

4. The optical system of claim 3, wherein the temporal delay is less than or equal to 15 ns.

5. The optical system of claim 3, wherein the plurality of optical elements further includes a second polarizer configured to combine the first polarized laser beam and the temporally delayed second polarized laser beam to form the modified pulsed laser beam.

6. The optical system of claim 2, wherein the first polarized laser beam comprises P polarization and the second polarized laser beam comprises S polarization.

7. The optical system of claim 2, wherein the optical system is configured to be operably coupled with a fiber bundle of a catheter,
   wherein the fiber bundle of the catheter has a higher damage threshold respective to transmitting the modified pulsed laser beam with a fluence greater than or equal to 50 millijoules per square millimeter (mJ/mm$^2$) and less than or equal to 80 mJ/mm$^2$ than respective to transmitting the pulsed laser beam with a fluence greater than or equal to 50 mJ/mm² and less than or equal to 80 mJ/mm², due at least in part to the temporal delay less than or equal to 15 ns between the second polarized laser beam and the first polarized laser beam.

8. The optical system of claim 1, wherein the optical system is configured to be operably coupled with a fiber bundle of a catheter,
wherein the modified pulsed laser beam is configured to be transmitted to the target tissue via the fiber bundle of the catheter for ablation of the target tissue, and
wherein the modified pulsed laser beam is configured to selectively ablate the target tissue by way of photomechanical ablation, photochemical ablation, or a combination thereof.

9. The optical system of claim 1, wherein the modified pulsed laser beam comprises a multi-peak waveform comprising a first peak and a second peak, and wherein the second peak is temporally separated from the first peak by less than or equal to 15 ns.

10. The optical system of claim 1, wherein the modified pulsed laser beam has a wavelength of 355 nanometers (nm).

11. An optical system in communication with a laser source for ablation of a target tissue, the optical system comprising:
a plurality of optical elements arranged to:
receive a pulsed laser beam from the laser source, wherein the pulsed laser beam comprises a beam propagation ratio (M2) greater than or equal to 10; and
form, based in part on the pulsed laser beam, a modified pulsed laser beam comprising:
a pulse width less than or equal to 25 nanoseconds (ns), and
a temporal delay between at least two component parts of the modified pulsed laser beam, the temporal delay equal to or less than a relaxation time of the target tissue.

12. The optical system of claim 11, wherein the plurality of optical elements includes a first polarizer configured to separate the received pulsed laser beam into a first polarized laser beam and a second polarized laser beam.

13. The optical system of claim 12, wherein the plurality of optical elements further includes at least one mirror arranged and configured to introduce the temporal delay into the second polarized laser beam.

14. The optical system of claim 13, wherein the temporal delay is less than or equal to 15 ns.

15. The optical system of claim 13, wherein the plurality of optical elements further includes a second polarizer configured to combine the first polarized laser beam and the temporally delayed second polarized laser beam into the modified pulsed laser beam.

16. The optical system of claim 15, wherein the first polarizer comprises a wave plate and the second polarizer comprises a thin film polarizer (TFP).

17. The optical system of claim 12, wherein the first polarized laser beam comprises P polarization and the second polarized laser beam comprises S polarization.

18. The optical system of claim 11, wherein the laser source comprises a Q-switched Nd:YAG laser source.

19. The optical system of claim 12, wherein the plurality of optical elements includes a mirror array arranged and configured to introduce the temporal delay into the second polarized laser beam.

20. The optical system of claim 11, wherein the modified pulsed laser beam has a wavelength of 355 nanometers (nm).

* * * * *